United States Patent

Vancaillie

[11] Patent Number: 5,486,173
[45] Date of Patent: Jan. 23, 1996

[54] SELF-GUIDING ELECTRODE AND CUTTING TIP FOR TISSUE RESECTION

[76] Inventor: Thierry G. Vancaillie, 133 Pin Oak Forest, San Antonio, Tex. 78232

[21] Appl. No.: 164,107

[22] Filed: Dec. 8, 1993

[51] Int. Cl.$^6$ .................................................. A61B 17/39
[52] U.S. Cl. .............................................. 606/45; 606/46
[58] Field of Search ............................... 606/45, 46, 48, 606/49, 50

[56] References Cited

U.S. PATENT DOCUMENTS

| | | | |
|---|---|---|---|
| 4,116,198 | 9/1978 | Roos | 606/46 |
| 5,196,011 | 3/1993 | Korth et al. | 606/46 |

FOREIGN PATENT DOCUMENTS

| | | | |
|---|---|---|---|
| 0419235 | 3/1991 | European Pat. Off. | 606/45 |
| 1548389 | 10/1968 | France | 606/46 |

OTHER PUBLICATIONS

C. J. G. Sutton, R. Macdonald, A. L. Magos, J. A. M. Broadbent, "Endometrial Resection," 'Endometrial Ablation,' Churchill Livingstone 1993, pp. 91–131.

*Primary Examiner*—Lee S. Cohen
*Attorney, Agent, or Firm*—Akin, Gump, Strauss, Hauer & Feld

[57] ABSTRACT

A self-guiding electrode and cutting tip for use in electrical tissue resection. Self-guiding forces are those applied substantially perpendicular to the longitudinal axis of an electrode, or rotationally about the longitudinal axis. Forces sufficient to compensate in part for errors in cutting tip placement are produced by tissue pressure acting on tissue skids and keels. Tissue skids are intended to slide along tissue surfaces, maintaining structures to which they are coupled at a substantially fixed spacing from the surface. Tissue keels are intended to slide between tissue planes, whether they are naturally occurring or a result of a surgical incision. Lateral deviations from a straight incision made in a plane substantially perpendicular to a tissue surface tend to be resisted by forces on a tissue keel affixed in a leading or following relationship with respect to a cutting loop. Deviations in depth tend to be reduced by maintaining substantially uniform tissue pressure on a tissue skid sliding on the surface. Rotational self-alignment and otherwise enhanced self-guiding characteristics may be achieved through employment of tissue skids and/or tissue keels in conjunction with one or more spring-centered joints placed in series with electrode conductors.

6 Claims, 1 Drawing Sheet

SELF-GUIDING ELECTRODE AND CUTTING TIP FOR TISSUE RESECTION

BACKGROUND

1. Field of the Invention

The invention relates to methods and apparatus for electrical resection of tissue.

2. Endoscopic Tissue Resection

Surgical tissue resection deep within body cavities may be performed either under direct vision or endoscopically with the aid of electrodes which are elongated (along a longitudinal axis) and thin enough to be inserted directly into the incision or placed through an endoscope. Notwithstanding their relatively small transverse dimensions, these electrodes comprise at least one insulated electrical conductor and commonly have two. Monopolar electrodes, which in use rely on a return current path through the patient's body, may have only one or a plurality of insulated electrical conductors. Bipolar electrodes, in contrast, provide a return current path through one or more insulated electrical conductors; hence bipolar electrodes commonly have two insulated conductors. Electrodes preferably additionally comprise an electrically energized electrode cutting loop tip (generally a wire which may be straight or bent into a curved, circular or oval shape). Electrodes having two insulated conductors, which may be either monopolar or bipolar, typically have cutting loops made of a length of wire bent into an open circular or oval loop shape and coupled to the conductors, one end of the wire loop coupled to each conductor.

Designed to be manipulated from outside a patient's body through a relatively small orifice or incision, an electrode cutting tip intended for endoscopic surgery may deflect significantly under the influence of relatively small lateral (bending) forces substantially perpendicular to the electrode's longitudinal axis or torsional (twisting) forces which act around the electrode's longitudinal axis. The surgeon counteracts any unintended deflections and otherwise guides the tip along a desired cutting plane by applying corrective forces while viewing the cutting tip movement through the endoscope.

Precise guidance of an electrode cutting tip along a predetermined cutting plane requires exceptional skill because of the restricted visibility offered by an endoscope and the relatively great distances separating the surgeon's hands from the tissue being resected. This is particularly true during electrical tissue resection because relatively small forces are sufficient to alter the path of an electrode cutting tip cutting through tissue. Such small forces, acting on the cutting tip at a point substantially distant from the surgeon's hand, are difficult for the surgeon to sense.

Adding to the difficulty of controlling movement of electrode cutting tips is the variety of forms the cutting tips may take, the type of tissue through which they are cutting, and the tip position with respect to existing tissue planes. An electrode cutting tip with self-guiding characteristics would tend to reduce both the incidence and range of erratic tip movement and also reduce the demands on the surgeon for guiding and correcting electrode movement. Such a self-guiding electrode would be particularly useful in surgical resection of tissue within the uterus, a roughly triangular organ in which portions of internal tissue surfaces lie in substantially parallel planes and comprise relatively uniform layers of substantially homogeneous tissue.

Greater accuracy in positioning the electrode cutting tip, in turn, would tend to reduce the time required for a variety of endoscopic surgical procedures while simultaneously increasing treatment efficacy. Reductions in cost and the likelihood of post-operative complications would naturally follow. Depending on the surgical site, electrode configuration, and tissues to be resected, various construction features related to self-guiding functions would be desirable.

SUMMARY OF THE INVENTION

The present invention relates to methods and apparatus for endoscopic tissue resection with electrically-energized electrodes having at least one self-guiding construction feature. Self-guiding electrodes of the present invention tend to achieve and/or maintain alignment or spacing of an electrode tissue cutting tip (e.g., a tissue-cutting loop) with respect to one or more tissue surfaces, and to at least partially compensate for small errors in forces applied to direct an electrode tissue cutting tip as it moves through tissue.

For convenience throughout the following discussion, forces will be described as having components in one or both of two orthogonal planes which contain the longitudinal axis of the distal portion of the endoscope through which the electrode is passed. The transverse plane is substantially parallel to the surface of tissue to be resected, and the depth plane is substantially perpendicular to the same tissue surface.

Electrical power is provided through an electrode to a tissue cutting tip of the present invention via one or more insulated conductors. An electrode tissue cutting tip, e.g., a tissue-cutting loop, is coupled to insulated conductors carrying electrical current from outside the body by loop coupling means which include, for example, welded or brazed junctions, screw terminals, snap-fit or friction-fit connectors. Thus, an electrode cutting tip of the present invention (comprising, e.g., a cutting loop) may be detachable (e.g. with screw terminals, snap-fit or friction-fit connectors) or substantially non-detachable (e.g., with brazed or welded connections) from the remaining portion of an electrode. For purposes of the present invention, an electrode will retain that designation even when temporarily separated (e.g., as in packaging for sale or sterilization) from an electrode cutting tip to which it would normally be attached in use.

To reach the tissue cutting loop, electric current may pass through one or more joints capable of rotation (including, in certain embodiments, loop coupling means) and/or one or more spring-centered joints, all such joints maintaining electrical continuity during relative movement across any such joint.

Forces applied by a surgeon to initially place a tissue cutting electrode tip may be transmitted substantially or entirely through the insulated conductors in certain preferred embodiments of the present invention. While the conductors may substantially stiffen an electrode against bending about an axis perpendicular to its longitudinal axis, electrodes preferably retain limited compliance in response to a lateral force (i.e., a force having component substantially perpendicular to the longitudinal axis), usually applied in the region of the cutting tip.

Note that the term lateral compliance indicates the degree of bending or deviation from a neutral (no-applied-force) position of an electrode in response to application of a lateral force component. This lateral compliance, which in certain embodiments arises from the resilience or shape-retaining qualities inherent in the insulated conductors themselves, is preferably in a range of values which would facilitate small cutting tip movements in response to tissue forces generated by self-guiding construction features of the electrodes. In certain embodiments, insulated conductors may comprise spring-centered joints which tend to return to a predetermined neutral position after deflection by a lateral force component. Spring-centered joints may comprise e.g., a series-connected (substantially colinear) coil or leaf spring or other resilient element which maintains or establishes a desired shape for the insulated conductor in the absence of external forces, while allowing temporary deformation of the conductor during application of a lateral force. Electrical continuity may be maintained directly through a spring-centered joint, or around the joint element(s) by an auxiliary conductor. Note that the degree of lateral compliance of a spring-centered joint may be made manually adjustable by, for example, providing an adjustable mechanical stop (e.g., a hollow tube which will slide over and mechanically link a portion of an insulated conductor and an adjacent portion of a spring-centered joint).

In preferred embodiments of electrodes having two conductors (e.g., one conductor coupled to each end of an electrically energized tissue-cutting loop), the distal portions of the two conductors proximate the cutting loop (i.e., the portion of each conductor adjacent the loop coupling means) may include one or more spring-centered joints in series (e.g., substantially colinearly) with the conductor to provide a desired level of lateral compliance. Election to include one or more spring-centered joints in each conductor of an electrode of the present invention will depend on the specific clinical use planned for the electrode, the degree of lateral compliance desired, and the inherent resilience of the electrode (without any joint) in response to lateral force applications. In certain applications, a series of spring-centered joints may be inserted substantially colinearly in the conductor(s) of an electrode with the joints having different compliancies in response to lateral forces. Such a series of joints may, in certain embodiments, provide a lateral compliance gradient to lateral force along the electrode longitudinal axis. For certain clinical applications, a gradient resulting in increasing lateral compliance toward the cutting tip may result in improved cutting tip control and/or enhanced self-guiding characteristics of the electrode.

To resist deformation and/or aid in establishing a desired level of lateral compliance of a two-conductor electrode primarily in the transverse plane, electrode electrical conductors may be coupled by a substantially planar stabilizer assembly lying between and coupled to the conductors, and substantially within the plane defined by the conductors in the region where they are coupled to the stabilizer. Components of lateral forces within the transverse plane will be resisted by the shear and bending strength of the stabilizer assembly, while lateral force components in the depth plane will be resisted to a lesser extent. The result will be an electrode with a substantially larger resistance to bending due to lateral force components in the transverse plane than to lateral force components in the depth plane. If a greater degree of self-guiding action is desired in the transverse plane for certain applications, shear and bending strength of the stabilizer assembly may be correspondingly reduced.

Self-guiding features of electrodes of the present invention relate to one or more tissue interfaces coupled to the electrode, each interface being capable of exerting lateral forces on the electrode as its electrode cutting tip moves through tissue. In preferred embodiments, a tissue interface may take the form of a substantially nonconductive skid coupled to the electrode (e.g., coupled to an electrode conductor, an electrode cutting tip loop, or to a conductor and cutting tip simultaneously). The tissue skid is a substantially planar member intended to slide over a substantially parallel portion of a tissue surface, and having sufficient surface area to transmit sufficient alignment force (arising from tissue pressure on the skid) to the electrode from the tissue to maintain a substantially fixed desired spacing of at least a portion of the electrode with respect to the tissue surface. Tissue skids may have a low-friction surface and/or rounded edges and/or a slightly convex configuration with respect to the tissue surface to facilitate sliding without materially deforming or damaging the tissue surface. Tissue may be substantially electrically non-conductive or substantially electrically conductive in whole or in part to facilitate application of electrical cutting and/or coagulation current waveforms to desired portions of the tissue surface.

Alignment force is transmitted from tissue contacted by a skid to the skid, and through the skid to the electrode via at least one skid coupling means. Skid coupling means include, for example, snap-fit, friction-fit, press-fit, clip-on, swaged on, or adhesively attached couplings, and the position of a skid coupling means on an electrode may be either adjustable or substantially non-adjustable in use. Certain preferred embodiments of the present invention allow manual or manually-directed adjustment of skid position on an electrode by, for example, a surgeon who wishes to change an existing tissue-cutting loop tissue resection depth to a greater or lesser depth.

Another form of tissue interface which may be coupled to electrodes of the present invention is a tissue keel, which is a substantially planar structure analogous to a tissue skid except that it is intended to slide between and be guided by adjacent tissue planes. The tissue planes may be naturally occurring or may be created by passage of, for example, a portion of an electrode cutting loop through the tissue. To facilitate sliding movement between closely spaced tissue planes, tissue keels characteristically have a substantially smaller cross-sectional area in a direction transverse to the intended direction of movement through the tissue than their cross-sectional area in a direction substantially parallel to the intended direction of movement through the tissue. To achieve any desired degree of self-guiding action, tissue keels preferably have sufficient cross-sectional area in a direction substantially parallel to the intended direction of movement through the tissue so that the requisite degree of self-guiding force may be applied to the keel without substantial deformation of adjacent tissue planes.

A tissue keel may be substantially nonconductive, in which case it would preferably be employed to pass through an existing passage (e.g., it might be coupled to and might follow a portion of a cutting loop as the loop passes through tissue). A tissue keel may also have a conductive leading edge (optionally with a tissue-cutting capability) backed by either a conducting or a substantially nonconducting planar keel structure, the planar keel structure being substantially coplanar with the leading edge. One or more tissue keels (having any desired combination of conductive or nonconductive leading edge and planar keel structure) may be coupled to a tissue cutting loop or analogous monopolar or bipolar tissue cutting structure, or to other portions of an electrode (e.g., to one or more conductors), or simultaneously to a tissue cutting structure and another portion of an electrode. One or more tissue keels may occupy only a portion or substantially all of the active cutting portion of such a tissue cutting loop or analogous structure.

Depending on the anatomic location of tissue to be resected and its surface conformation, tissue skids and keels may each be coupled to an electrode so as to be capable of exerting lateral forces during cutting tip movement in either the transverse plane, the depth plane or both. Appropriate placement of tissue skids and keels may also result in torsional forces useful in directing and/or positioning an electrode cutting tip. For example, a pair of tissue skids located on opposite sides of, and approximately equidistant from the electrode longitudinal axis, may act to maintain a cutting tip in a desired rotational orientation with respect to a tissue surface at the same time that the depth of penetration of the cutting tip into the tissue surface is being controlled. Such rotational self-alignment may be facilitated in certain preferred embodiments by inclusion of a rotational joint which can transmit bending and longitudinal forces, as well as electrical current, without attenuation. Where a variable degree of self-alignment action in the electrode is desired in different applications, transmission of rotational forces to an electrode cutting tip from the surgeon may be selectively attenuated or enhanced through an adjustable rotational joint.

Tissue skids and keels may be coupled to any portion of an electrode where application of lateral forces is desired. In preferred embodiments, skids may be coupled to each of two substantially parallel and insulated electrical conductors adjacent to the distal ends of the conductors. Preferred embodiments of the present invention include one or more tissue skids and/or one or more tissue keels coupled to an electrode without an attached electrode cutting tip, coupled to an electrode with an attached electrode cutting tip, or coupled to an electrode cutting tip without an attached electrode.

Preferred sizes for contact areas of tissue skids and keels may be determined depending on several factors, including the type of tissue to be resected, the size of the cutting tip, and the magnitude of lateral forces desired. Skids and keels exert reaction forces on tissue which are proportional to the lateral forces exerted on the electrode to which they are coupled. Effective positional control of the electrode therefore requires that pressures applied to tissues not cause significant displacement of the tissue adjacent to a skid or keel. For example, electrodes suitable for resection of endometrial tissue may have two skids within about 30 mm of a cutting loop with a total minimum skid tissue contact area preferably within a range of about 4 to 100 $mm^2$, depending in part on actual skid-loop distance. Skids immediately adjacent to a cutting loop in this application preferably have individual areas of about 10 $mm^2$.

Preferred embodiments of the present invention include an electrode, comprising at least one electrical conductor having a proximal end and a distal end and comprising coupling means for coupling a tissue cutting tip to said at least one electrical conductor proximate said distal end, and at least one tissue skid and/or at least one tissue keel coupled to said at least one electrical conductor proximate said distal end. The electrode thus described may additionally comprise a tissue cutting tip coupled to said at least one electrical conductor proximate said distal end. Note that the term distal refers to a position on the electrode or part thereof which is relatively farther from the source of electrical power than a position more proximal. Hence, for example, in electrodes of the present invention, a cutting tip (if present) will be distal to a planar stabilizer (if present).

Another preferred embodiment of the present invention is an electrode, comprising first and second electrical conductors and (optionally) a planar stabilizer assembly lying between and coupled to the first and second electrical conductors. Each of the conductors has a lateral compliance, a proximal end and a distal end, the first and second conductors being spaced apart and oriented proximal end to proximal end and distal end to distal end. Such an electrode further comprises a tissue cutting loop having first and second ends, coupling means for coupling said cutting loop first end to said first conductor distal end and said cutting loop second end to said second conductor distal end and at least one tissue skid and/or tissue keel coupled to each said first and second electrical conductor proximate each said distal end. Note that in various preferred embodiments, a tissue skid and/or tissue keel may be coupled to a cutting loop (and thence to an electrode conductor through coupling means), or the skid and/or keel may be directly coupled to an electrode conductor, or the skid and/or keel may be directly coupled to both an electrode conductor and to a cutting loop simultaneously. Use of the terms coupling or coupled without a modifier includes the possibility of either direct or indirect coupling or both.

An electrode of the present invention may additionally comprise at least one spring centered joint having a predetermined lateral compliance in series with each (or any) electrical conductor. The term predetermined means that the lateral compliance is established by the joint structure and materials and not necessarily that a specific value or range of values has been calculated, estimated or otherwise established for the lateral compliance. Thus, an electrode may comprise proximal and distal spring centered joints in series with each (or any) electrical conductor. Further, in an electrode having proximal and distal spring centered joints, the predetermined lateral compliance of each distal joint may substantially exceed the predetermined lateral compliance of each proximal joint, and the predetermined lateral compliance of each proximal joint may exceed the first conductor lateral compliance and/or the second conductor lateral compliance. This illustrates a method of providing a lateral compliance gradient in an electrode conductor, comprising coupling a plurality of spring centered joints in series with the electrode conductor, each said spring centered joint having lateral compliance greater than the conductor, and at least two said spring centered joints having non-identical lateral compliance.

Another preferred embodiment of the present invention is an electrode tissue cutting tip, comprising a wire loop and at least one tissue skid and/or tissue keel coupled to the wire loop. At least one tissue keel may be substantially electrically conductive in whole or in part and may be adapted (i.e., having suitable electrical pathways) to carry electrical currents for tissue cutting, coagulation, or both.

The electrodes and tissue cutting tips described herein reflect the application of methods of the present invention of making an electrode and/or tissue cutting tip at least partly self-guiding, comprising coupling at least one tissue keel and/or at least one tissue skid to the electrode and/or cutting tip. Also included are methods of increasing lateral compliance of an electrode conductor, comprising coupling at least one spring centered joint in series with the electrode conductor, each said spring centered joint having lateral compliance greater than the conductor.

DETAILED DESCRIPTION

Figure 1A:
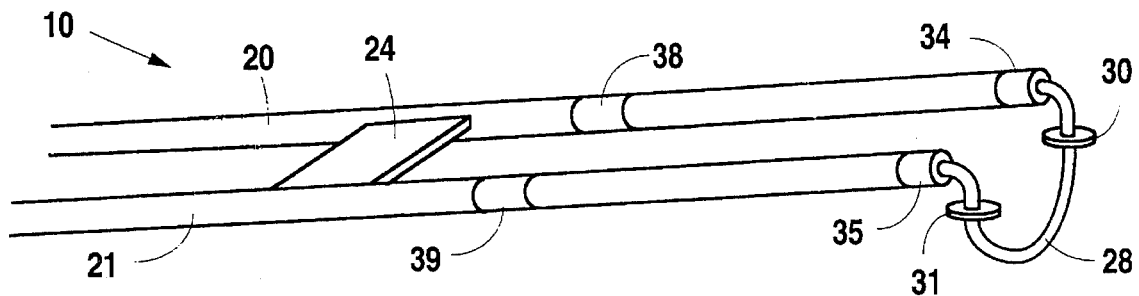
FIG. 1A schematically illustrates a two-conductor electrode with tissue cutting loop tip and two tissue skids coupled to the loop.

FIGS. 1A, 1B, 1C and 1D illustrate various embodiments 10,12,14,16 of two-conductor electrodes of the present invention. In each figure, the electrode longitudinal axis lies generally along the long dimension of the electrode, between conductors 20,21, and substantially equidistant from the conductors and parallel to them in the special case where conductors 20,21 are substantially parallel. Note that substantial parallelism of conductors 20,21 is not required in all embodiments of the present invention.

The two ends of cutting loop 28 are coupled to the respective insulated conductors 20,21 by coupling means 34,35, which in preferred embodiments may make the cutting loop 28 manually removable or, alternatively, substantially nonremovable. For example, coupling means 34,35 may comprise welded or brazed junctions, screw terminals, snap-fit or friction-fit connectors.

Also in each FIG. 1A, 1B, 1C and 1D, planar stabilizer assembly 24 is shown coupled to both insulated conductors 20,21 and lying substantially in the plane of insulated conductors 20,21. Note that conductors 20,21 are not required to be coplanar throughout their length, but will typically be substantially coplanar for a portion of their length which includes the coupling to planar stabilizer assembly 24. Stabilizer assembly 24 acts to substantially maintain a predetermined spacing between conductors 20,21 for at least a portion of their length while resisting bending (i.e., decreasing lateral compliance) of conductors 20,21 in response to lateral force components (i.e., force components substantially perpendicular to the electrode longitudinal axis) within the plane of planar stabilizer assembly 24. Stabilizer assembly 24 also (analogously) reduces lateral compliance of conductors 20,21 in response to lateral force components outside the plane of planar stabilizer assembly 24, but generally to a different (and usually lesser) extent than lateral compliance reductions within the plane of planar stabilizer assembly 24.

Spring-centered joints 38,39 are in series with (i.e., substantially colinear with) conductors 20,21, and act to increase lateral compliance of conductors 20,21 in the region between joints 38,39 and coupling means 34,35, thus facilitating proper orientation of cutting loop 28 with respect to a tissue surface. If, for example, electrode 10, 19 14 or 16 is applied to a tissue surface (not shown), joints 38,39 allow some angular misalignment (i.e., non-parallelism) between the plane of stabilizer assembly 24 and the transverse plane at the tissue surface. Coupling means 34,35 will preferably lie substantially within or adjacent to (and substantially equally spaced from) the transverse plane at the tissue surface, and they may do so in spite of the above misalignment if joints 38,39 act to allow individual adjustment of the position of coupling means 34,35. Note that adjustment of electrodes 10, 12, 14 and 16 to the above misalignment may also require some bending of cutting loop 28 and/or rotation of coupling means 34,35 with respect to insulated conductors 20,21 respectively, either or both of the bending and/or rotating actions occuring while electrical continuity is maintained through cutting loop 28.

The at-least-partly self-guided response of electrode 10 to misalignment (nonparallelism) between the plane of stabilizer assembly 24 and the transverse plane at a tissue surface to be resected (not shown) is facilitated by lateral (reaction) forces acting from the tissue surface to tissue skids 30,31, and thereby to cutting loop 28, and thereby to coupling means 34,35, and thereby to conductors 20,21 respectively. Misalignment as described in this paragraph causes, in general, either tissue skid 30 or tissue skid 31 to contact a tissue surface first as cutting loop 28 is applied to the surface. Because of such non-simultaneous tissue skid contacts, the conductor 20 or 21 which is proximate the first-contacting tissue skid would tend to be displaced (due to its lateral compliance) to a greater extent than the conductor 20 or 21 which is proximate the second-contacting tissue skid. Such displacement will thus act to bring tissue skids 30,31 into substantially simultaneous contact with a tissue surface, thereby effectively self-guiding cutting loop 28 into proper orientation with respect to a tissue surface.

Figure 1B:
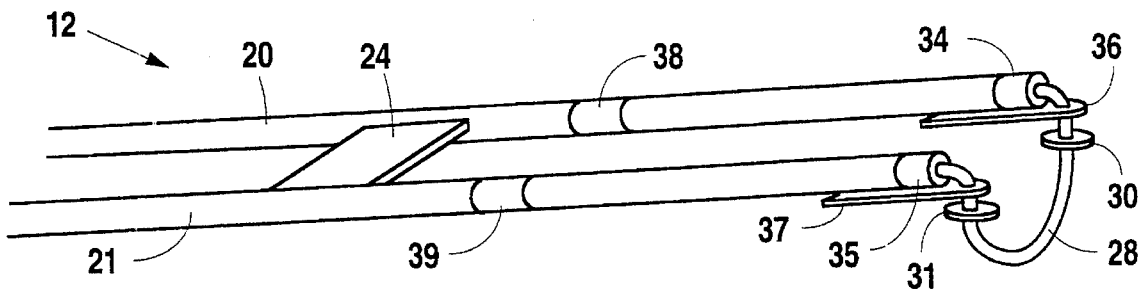
FIG. 1B schematically illustrates a two-conductor electrode with tissue cutting loop tip, two tissue skids coupled to the loop and respective conductors, and two additional tissue skids coupled to the loop.

Analogously, electrode 12 may be at-least-partly self-guided to a proper orientation with respect to a tissue surface (i.e., an orientation in which tissue skids 30,31 are in substantially simultaneous contact with the tissue surface) by an action similar to that described above. Note that tissue skids 30,31 are shown in FIG. 1B in positions wherein they will substantially prevent tissue surface contact with tissue skids 36,37. But cutting loop 28 of electrode 12 may operate at a tissue-cutting depth established by tissue skids 36,37 if either cutting loop 28 is replaced with a cutting loop having no tissue skids attached, or if tissue skids 30,31 are removed or readjusted to a position on cutting loop 28 where they would be adjacent tissue skids 36,37. Because tissue skids 30,31 are, in certain preferred embodiments, manually adjustable and/or removable from cutting loop 28, any of the above options may be elected.

Figure 1C:
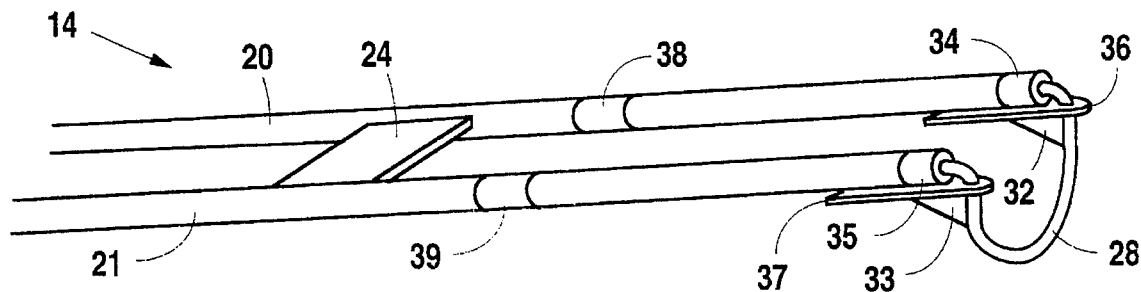
FIG. 1C schematically illustrates a two-conductor electrode with tissue cutting loop tip, two tissue skids coupled to the loop and to the conductors, and two tissue keels coupled to the loop and to the conductors.

Electrode 14 in FIG. 1C illustrates how self-guiding forces may be applied according to the present invention substantially simultaneously in both transverse and depth planes. Self-guiding forces substantially active in the depth plane may be applied through tissue skids 36,37, while self-guiding forces substantially active in the transverse plane may be applied through tissue keels 32,33, which may be alternatively coupled to cutting loop 28, tissue skids 36,37 respectively, or (as shown in FIG. 1C) both cutting loop 28 and the respective tissue skids. Because tissue keels 32,33 may lead cutting loop 28 in passing through tissue, tissue keels 32,33 (or at least the leading edges thereof) would preferably be electrically conductive and energized by the same electrical source as cutting loop 28.

Figure 1D:
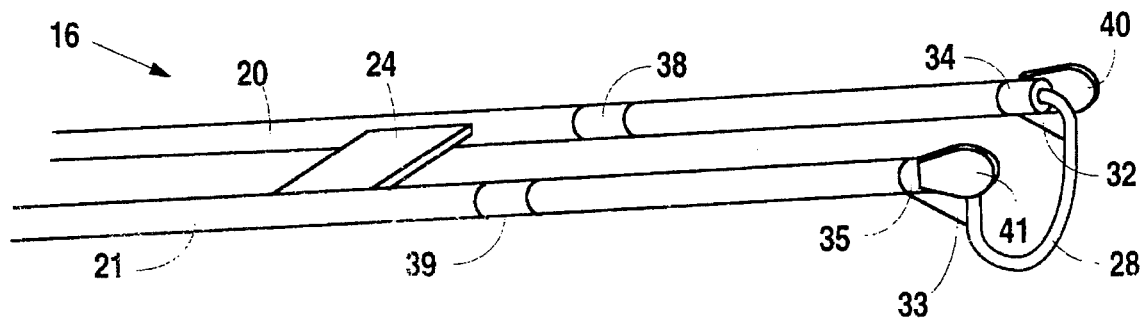
FIG. 1D schematically illustrates a two-conductor electrode with tissue cutting loop tip, two tissue keels coupled to the conductors laterally, and two tissue keels coupled to the loop and the conductors.

FIG. 1D illustrates an analogous configuration of an electrode of the present invention wherein tissue keels 32,33 may be alternatively coupled to cutting loop 28, coupling means 34,35 respectively, or (as shown in FIG. 1D) both cutting loop 28 and the respective coupling means. Because tissue keels 32,33 may lead cutting loop 28 in passing through tissue, tissue keels 32,33 (or at least the leading edges thereof) would preferably be electrically conductive and energized by the same electrical source as cutting loop 28. As may be appreciated from FIG. 1D, however, tissue keels 40,41 substantially follow tissue keels 32,33 and cutting loop 28 through tissue being resected. Thus, tissue keels 40,41 may be electrically non-conductive in whole or in part, and may be configured to carry to contacting tissue planes electrical currents for cutting, coagulation or both.

What is claimed is:

1. An electrode, comprising first and second electrical conductors, each said conductor having a lateral compliance, a proximal end and a distal end, said conductors being spaced apart and oriented proximal end to proximal end and distal end to distal end;

at least one spring centered joint having a predetermined lateral compliance in series with each said first and second electrical conductor;

a tissue cutting loop having first and second ends;

coupling means for coupling said cutting loop first end to said first conductor distal end and said cutting loop second end to said second conductor distal end; and at least one tissue skid coupled to each said first and second electrical conductor proximate each said distal end.

2. The electrode of claim 1 comprising proximal and distal spring centered joints in series with each first and second electrical conductor.

3. The electrode of claim 2 wherein said predetermined lateral compliance of each said distal joint substantially exceeds said predetermined lateral compliance of each said proximal joint, and said predetermined lateral compliance of each said proximal joint exceeds said first conductor lateral compliance and said second conductor lateral compliance.

4. An electrode, comprising first and second electrical conductors, each said conductor having a lateral compliance, a proximal end and a distal end, said conductors being spaced apart and oriented proximal end to proximal end and distal end to distal end;

at least one spring centered joint in series with each said first and second electrical conductor;

a tissue cutting loop having first and second ends;

coupling means for coupling said cutting loop first end to said first conductor distal end and said cutting loop second end to said second conductor distal end; and at least one tissue keel coupled to each said first and second electrical conductor proximate each said distal end.

5. The electrode of claim 4 comprising proximal and distal spring centered joints in series with each first and second electrical conductor, each joint having a predetermined lateral compliance.

6. The electrode of claim 5 wherein said predetermined lateral compliance of each said distal joint substantially exceeds said predetermined lateral compliance of each said proximal joint, and said predetermined lateral compliance of each said proximal joint exceeds said first conductor lateral compliance and said second conductor lateral compliance.

* * * * *